(12) United States Patent
Vasilevskis et al.

(10) Patent No.: US 6,288,224 B1
(45) Date of Patent: Sep. 11, 2001

(54) PREPARATION OF N-ARYLMETHYL AZIRIDINE DERIVATIVES, 1,4,7,10-TETRAAZACYCLODODECANE DERIVATIVES OBTAINED THEREFROM AND N-ARYLETHYL-ETHANOLAMINE SULPHONATE ESTERS AS INTERMEDIATES

(75) Inventors: Janis Vasilevskis; John Varadarajan; Martha Garrity; Jere Douglas Fellmann, all of Wayne, PA (US); Louis Messerle; Gandara Amarasinghe, both of Iowa City, IA (US)

(73) Assignees: Nycomed Salutar, Inc., Wayne, PA (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/546,430

(22) Filed: Apr. 10, 2000

Related U.S. Application Data

(62) Division of application No. 08/894,790, filed as application No. PCT/GB96/00552 on Mar. 8, 1996, now Pat. No. 6,048,979.

(30) Foreign Application Priority Data

Mar. 10, 1995 (GB) .................................... 9504921
Dec. 28, 1995 (GB) .................................... 9526616

(51) Int. Cl.$^7$ ................................................ C07D 257/02
(52) U.S. Cl. ............................................................ 540/474
(58) Field of Search ............................................. 540/474

(56) References Cited

U.S. PATENT DOCUMENTS 3,828,023  8/1974  Cornier et al. ..................... 260/239
4,093,615  6/1978  Ham et al. ........................... 260/239

FOREIGN PATENT DOCUMENTS 665 790    10/1938  (DE) .
0 292 689   4/1988  (EP) .
1 022 212   3/1966  (GB) .
1 529 150  10/1978  (GB) .

OTHER PUBLICATIONS

518. Cyclic imines from aminoalcohols, in: "Synthetic Methods of Organic Chemistry," vol. 6 (Theilheimer W., Ed.), 1952, pp. 186–187.
Aliev et al., *European Polymer Journal*, vol. 16, No. 8, Jan. 1, 1980, pp. 679–688.
Goethals et al., *Polymer Bulletin*, vol. 6, No. 11/12, 1981, pp. 121–126.
Deyrup, Aziridines, chapter I, in: Small ring heterocycles, part 1, aziridines, azirines, thiiranes, thiirenes (Hassner, A., Ed.), 1983, *Interscience*, pp. 11–13.

Backes, Aziridine, in: "Methoden der organischen Chemie (Houben–Weyl) Band E16c Organische Stickstoff–Verbindungen III" (Klamann, D., Ed.), 1992, *Georg Thieme Verlag*, pp. 394–397.

Hansen et al., *Journal of Heterocyclic Chemistry*, vol. 5, No. 2, Apr. 1968, p. 305.

Brunner et al., *Supramolecular Chemistry*, vol. 2, No. 2–3, 1993, pp. 103–110.

Kuschmiers et al., *Chemical Abstracts*, vol. 101, No. 8, Aug. 20, 1984, abstract No. 63594w.

Hansen et al., The Unique Synthesis of . . . , J. Heterocyclic Chem., 5:305, Apr. 1968.

*Primary Examiner*—Laura L. Stockton
(74) *Attorney, Agent, or Firm*—Bacon & Thomas

(57) ABSTRACT

Aziridines may be subjeted to a cyclooligomerization reaction to produce polyazacycloalkane compounds useful for example in the preparation of chelating agents for use in diagnostic imaging contrast agents. N-benzyl-aziridine in particular is useful as it can be cyclotetramerized and debenzylated to yield cyclen, a key intermediate in chelating agent preparation. The invention provides a particularly attractive route to production of N-benzyl and other N-arylmethyl aziridines of formula (I)

(I)

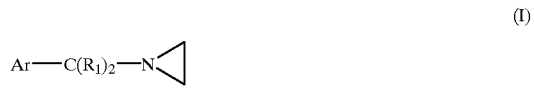

where each $R_1$ is independently hydrogen or a group AR and Ar is an optionally substituted phenyl group. The process comprises reacting a purified N-arylmethylethanolamine-sulphonate sulphonate ester with a base. N-aryimethyl-ethanolamine sulphonate ester of the formula $R'NHCH_2CH_2OSO_3H$, wherein the N-arylmethyl group R' is an N-(bisarylmethyl) or N-(triarylmethyl) group, as intermediates. In a further aspect, the invention provides compounds of formula (II)

(II)

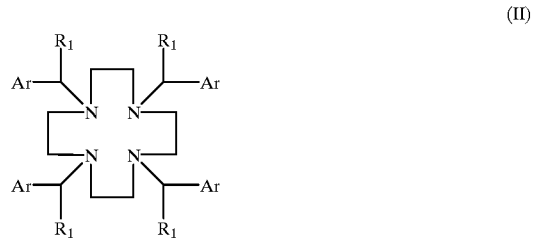

where Ar and $R_1$ are as hereinabove defined and at least two differing $ArCHR_{21}$ moieties are present.

3 Claims, 3 Drawing Sheets

PREPARATION OF N-ARYLMETHYL AZIRIDINE DERIVATIVES, 1,4,7,10-TETRAAZACYCLODODECANE DERIVATIVES OBTAINED THEREFROM AND N-ARYLETHYL-ETHANOLAMINE SULPHONATE ESTERS AS INTERMEDIATES

This application is a divisional application of U.S. application Ser. No. 08/894,790 filed Dec. 2, 1997, which will issue as U.S. Pat. No. 6,048,979 on Apr. 11, 2000, which is a 371 of International application PCT/GB96/00552, filed Mar. 8, 1996.

This invention relates to a novel process for the preparation of N-arylmethyl-aziridines, in particular N-benzyl-aziridine and N-benzhydryl-aziridine, and to the use of such aziridines.

In the field of magnetic resonance imaging, various lanthanide chelates of cyclen-derivative macrocyclic chelating agents have been proposed. Two, GdHP-DO3A (ProHance from Squibb) and GdDOTA (Dotarem from Guerbet), are available commercially. These macrocyclic chelating agents form particularly stable chelate complexes with the contrast-generating paramagnetic metal ions and thus are suitable carriers for the metal ions to ensure appropriate biodistribution and elimination.

Cyclen itself (1,4,7,10-tetraazacyclododecane) is a key and somewhat expensive intermediate in the preparation of these macrocyclic chelants.

Cyclen's tetraaza macrocycle can be prepared by a variety of synthetic routes, for example via diamine:diamine or triamine:monoamine cyclic condensations such as are described by Tweedle in EP-A-232751 and EP-A-292689. However in 1968 Hansen et al reported that tetrabenzylcyclen could be produced in good yield by cyclo-tetramerization of N-benzyl-aziridine.

The reaction described by Hansen et al in J.Heterocycl. Chem 5:305 (1968) involved refluxing a mixture of 10 g of N-benzyl-aziridine and 0.05 g of p-toluenesulphonic acid (PTSA) in 75 ml of 95% alcohol for six hours.

Cornier et al (in U.S. Pat. No. 3,82,8,023) and Ham (in a chapter entitled "Polymerization of Aziridines" in "Polymeric Amines and Ammonium Salts", Ed. Goethels, Pergamon, 1980) confirmed that cyclo-tetramerization of arylmethyl-aziridines occurs. Tsukube in J. Chem. Soc. Perkin Trans I 1983, 29–35 reported high yields for tetra-N-benzyl-cyclen using acid-catalysed cyclotetramerization of N-benzyl-aziridine using the reaction conditions of Hansen (supra).

Arylmethyl groups, such as benzyl groups, are frequently used as protecting groups in organic syntheses and selective removal of such groups represents straightforward chemistry. Since in this fashion the ring nitrogens of a tetra-(N-arylmethyl)-cyclen can be "deprotected" to yield cyclen, N-arylmethyl-azirdne tetramerizarion offers a simple and attractive route in the preparation of macrocyclic chelating agents for use in diagnostic contrast agents.

Several methods for the production of the N-arylmethyl-aziridine starting materials are known in the literature. Thus Appel et al in Chem Ber 107:5–12 (1974) describe the reaction of N-benzylethanolamine with triethylamine, carbon tetrachloride and triphenylphosphine:

$(C_6H_5)_3P+CCl_4+N(C_2H_5)_3+C_6H_5CH_2NHCH_2CH_2OH \rightarrow (C_6H_5)_3$
$PO+CHCl_3+HN(C_2H_5)_3Cl+C_6H_5CH_2-N\triangleleft$ Appel et al reported a yield of 66% for this reaction. However repeating the process using N-benzylethanolamine supplied by Aldrich, yields of only 39 to 45% were obtained.

The best results were obtained when extra extraction steps were employed and the crude extract solution was combined with solid KOH before and during the rotary evaporation. The Appel process moreover has a number of severe disadvantages, including (1) the generation of large quantities of $(C_6H_5)_3PO$ and $HN(C_2H_5)_3Cl$ as by-products, (2) the use of carbon tetrachloride a material becoming increasingly expensive and difficult to use as a result of environment protection regulations, and (3) the lengthy reaction time of 14 hours, the necessity for temperature control at 12° C. during cyclization and the overall synthesis and work up time of about three days.

Pfister, in Synthesis 969–970 (1984), described a one-pot synthesis involving reaction of N-benzylethanolamine, triphenylphosphine and diethylazodicarboxylate:

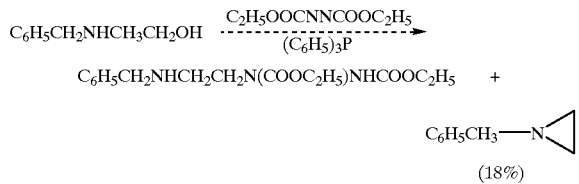

This reaction however gave only a very poor yield of 18%.

In 1969, Lanclois et al in Tetrahedron Letters 25: 2085–2088 (1969) reported a two-step synthesis from benzylamine:

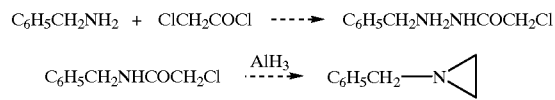

Again however the yield at 45% was poor.

In U.S. Pat. No. 3,855,217. Thill proposed the production of N-benzyl-aziridine by the reaction of aziridine itself with a benzyl halide. The same process was reported by Tsukube (supra) While the reported yields were good, the use of aziridine as a starting material is highly undesirable. Thus the entry for aziridine in The Merck Index, 11th Edition, page 600, 1989 carries the caution "Strongly irritating to eyes, skin, mucous membranes. Can be a skin sensitizer. This substance has been listed as a carcinogen by OHSA. Fed. Reg. 39, 3757 (1974)."

Thus there is a need for a simpie, environmentally acceptable and yet good yield process for N-arylmethylaziridine production which will yield a product suitable for use in a cyclo-tetramerization reactions to yield tetra(arylmethyl) cyclen.

We have now found that such a process is provided by the treatment of a purified N-(arylmethyl)ethanolamine-sulphonate ester with a base. The sulphonate ester itself can be prepared by treatment of an N-arylmethyletheanolamine with sulphuric acid and this optionally is an initial step in the process of the invention.

Thus, viewed room one aspect, the invention provides a process for the preparation of an N-aryimethyl-aziridine of formula I $$Ar-C(R_1)_2-N\triangleleft \qquad (I)$$

(where each $R_1$ independently is hydrogen or a group Ar and Ar is an optionally substituted phenyl group), said process comprising reacting a purified N-arylmethylethanolamine-sulphonate ester with a base.

In the N-arylmethyl-aziridines prepared according to the invention, preferably one $R_1$ group is hydrogen, and especially preferably both are hydrogen. Particularly preferably, the product of the process of the invention will be N-benzyl-aziridine or N-benzhydryl-aziridine, the compounds of formula I where Ar is an unsubstituted phenyl group.

As mentioned above, the process of the invention optionally includes the precursor step of generation of the sulphonate ester by reaction of an N-arylmethylethanolamine with sulphuric acid. The N-arylmethyethanolamine starting compound if not available commercially can readily be prepared by reaction of the corresponding arylmethylamine with 2-chloroethan-1-ol.

The N-(bisarylmethyl)-ethanolamine sulphonate esters and the N-(triarylmethyl)-ethanolamine sulphonate esters are themselves novel compounds and form a further aspect of the present invention.

Generation of the sulphonate ester is preferably carried out in a solvent, for example water at a temperature in the range 80 to 150° C., for example 50 to 100° C. The acid concentration used is preferably 7.25 to 8 molar, especially about 7.7 molar and the acid and N-(arylmethyl) ethanolamine reagents are conveniently used in a molar ratio of about 1:1. The reaction is relatively rapid, and may take only a matter of seconds to yield the sulphonate ester.

Where the ester is to be isolated (i.e. purified) before reaction with the base, this may be done by softening the solid mass with ethanol, grinding with ethanol, filtering and drying. In this way yields of 74% of a very pure product have been obtained.

Isolation of the sulphonate ester is straightforward since the ester precipitates out of aqueous solution.

The base used in the process of the present invention may be an organic or inorganic base, preferably an alkali metal hydroxide such as sodium hydroxide.

Reaction with the base is preferably effected in a solvent or solvent mixture, e.g. water. Solutions of the base and the sulphonate ester may be rapidly mixed to produce a reaction mixture. The reaction is conveniently effected at elevated temperature, e.g. 50 to 150° C., especially about 80° C., and for a period of 1 to 5 hours, particularly 2 to 3 hours.

The N-arylmethyl-aziridine product can be taken up in an organic solvent such as ether and subsequently isolated by solvent distillation, preferably in the presence of an acid neutralizing agent, e.g. KOH pellets.

Since the stability of the N-arylmethyl-aziridine seems to be reduced by the presence of N-arylmethylethanolamine, it is important that the product should be distilled carefully and stored over an acid neutralizing agent (preferably KOH) if it is not to be used immediately for cyclo-tetramerization.

Product removal from the reaction mixture is preferably effected during the reaction with the base, for example by steam distillation. However this may require fresh solvent (water) to be added to the reaction mixture if the reagents show signs of crystallizing out. The product may be removed from the distillate by solvenr layer separation, organic solvent (ether) extraction of the aqueous phase, combination and drying of the organic phases, and removal of the organic solvent by rotary evaporation in the presence of KOH and vacuum distillation in the presence of KOH.

By these methods, yields of 85% of N-benzylaziridine (relative to the sulphonate ester) have been achieved.

The overall reaction scheme may thus for example be:

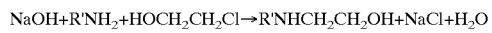
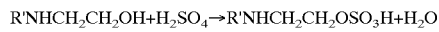

where R' is the arylmethyl group.

The sulphonate ester formation and subsequent base treatment give as their only by-products water and sodium sulphate, both innocuous materials.

The process of the present invention thus has several significant advantages over the prior art syntheses, in particular the avoidance of undesirable solvents such as carbon tetrachloride, the generation only of innocuous by-products, the non-necessity for temperature control during the cyclization step, the short preparation and work-up times, the production of a highly pure product, and the good yields obtained.

As mentioned above, it is known that N-arylmethylaziridines can be cyclo-tetramerized to yield tetra-(N-arylmethyl)-cyclens. However the use of the resulting cyclic tetramers for the generation of cyclen itself for subsequent use in the product of macrocyclic chelating agents has not previously been proposed. Thus viewed from a further aspect, the present invention also provides the use of N-arylmethylaziridines for the manufacture of cyclen and cyclenbased macrocyclic chelants and chelates thereof. Viewed from a yet further asdect, the invention also provides a method of preparation of cyclen and cyclen derivatives comprising (i) cyclo-tetramerizing an N-arylmethyl-aziridine; (ii) cleaving arylmethyl groups from the resulting cyclen derivative; (iii) optionally, N-alkylating the resulting product; and (iv) optionally, metallating the N-alkylated product.

Step (i) above is preferably effected in a solvent and in the presence of an acid catalyst. As the solvent there may for example be used water, methanol, ethanol, propanol, butanol, acetonitrile, dichloromethane, 1,2-dichloroethane, toluene or mixtures thereof. Ethanol however is preferred. As the catalyst, $BF_3$, or strong protic acids such as $H_2SO_4$, $H_3PO_4$ and HCl or acidic macroreticular resins such as Amberlyte XN-1010 and Amberlyte 15 may be used but PTSA is preferred, especially at 0 to 10% by weight relative to the aziridine, particularly 2 to 7% and more particularly 2.5 to 3.5% by weight. The reaction is preferably effected at elevated temperatures, e.g. 50 to 150° C., especially 60 to 80° C. or under reflux.

The initial aziridine concentration is preferably in the range 0.01 to 5M, especially 0.1 to 2M and particularly about 0.5M or about 1M as in this way the yield of the N-protected cyclen is optimized.

The reaction is preferably effected for less than 20 hours, e.g. 2 to 10 and especially about 6 hours as increasina the reaction time causes an increase in production of undesired dimers.

The aziridine used in step (i) may be a single compound; however alternatively a mixture of arylmethyl-aziridines may be used to produce a heteroprotected cyclen. In this regard, mixtures of N-benzyl-aziridine and N-benzhydryl-aziridine are particularly preferred. The resulting hetero-protected cyclens are novel compounds and form a further aspect of the invention. Thus, viewed from this aspect the invention provides compounds of formula II

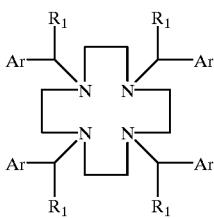

(II)

where Ar and $R_1$ are as hereinbefore defined and at least two differing ArCHR$_1$ moieties are present.

In the compounds of formula II, it is particularly preferred that either one ArCHR$_1$ moiety is benzyl and the other three are benzhydryl or that one is benzhydryl and the other three are benzyl. Since debenzylation and debenzhydrylation can be performed relatively selectively, such compounds have great potential as intermediates in the production of cyclen derivatives having three nitrogens substituted by one form of substituent and the fourth by a different substituent, for example as in DO3A and HPDO3A and as in the DO3A dimers recently proposed by Nycomed Salutar and by Schering as chelants for high relaxivity MR contrast agents.

Where heterotetramerization is desired, step (i) will be performed using the different aziridines in molar ratios such as to give the optimum yield of the desired substitution pattern. The optimum ratio can be determined by simple trial experimentation beginning with molar ratios corresponding to the ratio of the corresponding arylmethyl groups in the desired end product.

Step (ii) may be effected using standard amine deprotection techniques, for example reductive deprotection over a metal catalyst. Where benzyl and benzhydryl protective groups are present, reductive deprotection may selectively remove the benzyl groups first Particularly conveniently, reductive deprotection may be effected by hydrogenation over a palladium/charcoal catalyst. Alternatively, one may use cyclohexene and a palladium/charcoal catalyst If desired, partial deprotection may be effected by limiting the quantity or activity of reductant used so as to yield for example monoprotected or tri-protected cyclen. Alkylation of such partially deprotected cyclens can be followed by further deprotection and if desired further N-alkylation steps to yield heteroalkylated cyclen derivatives such as DO3A or HPDO3A.

Step (iii), the N-alkylation step, can be used to introduce desired alkyl or substituted alkyl groups on to the macrocyclic skeleton and again conventional alkylation techniques may be used, for example involving reaction with an alkyl halide $R_2$-Hal (where Hal is a halogen atom such as chlorine ox bromine and $R_2$ is an alkyl group optionally substituted, for example by hydroxy, alkoxy or aryl groups or by chelant moieties, such as carboxamide or phosphonamide groups or carboxyl or phosphonic acid groups (optionally protected by ester groups)) or $R_2$ may be an amphiphilic aralkyl group comprising a N, S, O or P interrupted $C_{2-25}$ alkylene chain, e.g. a polyalkylene oxide chain. The alkyl or alkylene moieties in $R_2$ will, unless otherwise stated, conveniently contain 1 to 12, preferably 1 to 6, carbon atoms and any chelant moiety will preferably be on the alpha or beta carbon. If a protected chelant group is introduced in this fashion, it may subsequently be deprotected, for example by ester cleavage to make the group available for metallation.

Where $R_2$ is an amphiphilic group, it may for example be a group L—Ar$^1$(—AH)$_n$ where each L is an $C_{2-25}$-alkylene linker wherein at least one CH$_2$ moiety is replaced by X$^1$ or a group $X^1(CH_2CH_2X^1)_u$ (where u is a positive integer) such as $X^1CH_2CH_2X^1$, $X^1CH_2CH_2X^1CH_2CH_2X^1$, $X^1CH_2CH_2X^1CH_2CH_2X^1CH_2CH_2X^1$, etc), and wherein L is optionally interrupted by a metabolizable group M but with the provisos that the terminus of L adjacent the cyclen ring is CH$_2$ and that the terminus of L adjacent Ar$^1$ is X$^1$ or a CH$_2$ group adjacent or separated by one CH$_2$ from a group X$^1$ (thus for example the L—Ar$^1$ linkage may be $L^1$—$X^1$—Ar$^1$, $L^1$—CH$_2$—Ar$^1$, $L^1$—$X^1$CH$_2$—Ar$^1$ or $L^1$—$X^1$CH$_2$CH$_2$—Ar$^1$, where $L^1$ is the residue of L);

each Ar$^1$ is an aryl ring optionally substituted by or having fused thereto a further aryl ring;

each AH is a protic acid group, preferably an oxyacid, e.g. a carbon, sulphur or phosphorus oxyacid or a salt thereof;

each X$^1$ is O, S, NR$_3$ or PR$_3$;

each R$_3$ is hydrogen, alkyl or aryl;

and n is a positive integer for example 1, 2 or 3.

Metallation in step (iv) may also be effected by conventional methods, for example as described in the patent literature relating to MR contrast agents (see for example EP-A-71564, EP-A-130934, EP-A-165728, EP-A-258616 and WO-A-86/06605.

The choice of metal ions to be complexed will depend upon the intended end use for the chelate complex. Especially preferred are ions of metals of atomic numbers 22 to 32, 42 to 44, 49 and 57 to 83, in particular Gd.

Where the chelate is to be used as an MR contrast agent, the chelated metal species is conveniently a paramagnetic ion of a transition metal or a lanthanide, preferably having an atomic number of 21 to 29, 42, 44 or 57 to 71. Complexes of Eu, Gd, Dy, Ho, Cr, Mn and Fe are especially preferred and Gd$^{3+}$, Mn$^{2+}$ and Dy$^{3+}$ are particularly preferred ions. For use as contrast agents in MRI, the paramagnetic metal species is conveniently non-radioactive as radioactivity is a characteristic which is neither required nor desirable.

Where the chelate complex is to be used as an X-ray or ultrasound contrast agent, the metal is preferably a heavy metal such as a non-radioactive metal with an atomic number greater than 37, preferably greater than 50, for example Dy$^{3+}$.

Where the metal complex is to be used in scintigraphy or radiotherapy, the chelated metal species must of course be radioactive and any conventional complexable radioactive isotope, such as $^{99m}$Tc or $^{111}$In for example may be used. For radiotherapy the chelated metal may for example be $^{153}$SM, $^{67}$CU or $^{90}$Y.

The aziridine tetramerization reaction can if desired be driven by removal of the tetramer and re-equilibration of the remaining fluid reaction mixture. While a tetra-(N-arylmethyl)-cyclen tetramer product will generally precipitate out, cyclic tetramers produced using other aziridines may be caused to separate out, e.g. by metallation, for example with nickel or calcium or other appropriately sized metal ions, whereupon the remaining reaction mixture may be re-equilibrated for example by heating with an acid, generally a strong acid. Thus viewed from a further aspect the invention provides a process for aziridine cyclotetramerization which process comprises oligomerizing an aziridine (preferably but not necessarily an arylmethylaziridine), separating a cyclic tetramer product from the reaction mixture, heating the residual reaction mixture with an acid, and separating out further cyclic tetramer product from the reaction mixture. Re-equilibration may be effected repeatedly to increase tetramer yield.

In the cyclooligomerization process, using N-benzyl-aziridine the most prominent cyclooligomer product is 1,4, 7,10-tetra(N-benzyl)-tetraazacyclo-dodecane, and the next most predominant product present in the reaction mixture is 1,4,7,10,13-penta(N-benzyl)-pentaazacyclopentadecane. The presence of this was confirnmed by GPC co-injection of an authentic sample of 1,4,7,10,13-penta(N-benzyl)-pentaazacyclo-pentadecane.

The cyclization reaction can be steered towards the production of other cyclic oligomers than the tetramer by modification of the reagents and process conditions, eg. the TACN trimer or the cyclic pentamer. By appropriate selection of the pH and the arylmethyl groups in the aziridine reagents, one can control the optimal ring size and substitution pattern in the cyclooligomeric product. Thus different arylmethyl groups produce different distributions of cyclic oligomers. For example, using N-benzhydryl aziridine one obtains a substantial yield of the cyclic pentamer. Moreover, it has been found that pH modification, e.g. by protonation of the aziridine reagent, or a portion thereof for example 25%, can result in the cyclic trimers and pentamers being produced in reasonable yield. The cyclic trimers and pentamers are of considerable commercial interest and this process for their preparation is a further aspect of the present invention. Viewed from this aspect the invention provides a process for aziridine oligomerization (preferably but not essentially of N-arylmethyl aziridines) which process comprises cyclooligomerizing an at least partially protonated aziridine and collecting the cyclic ventamer thus formed.

All patent and scientific publications mentioned above are incorporated herein by reference.

The invention is illustrated further by reference to the following non-limiting Examples and to the accompanying drawings in which.

Figure 1:
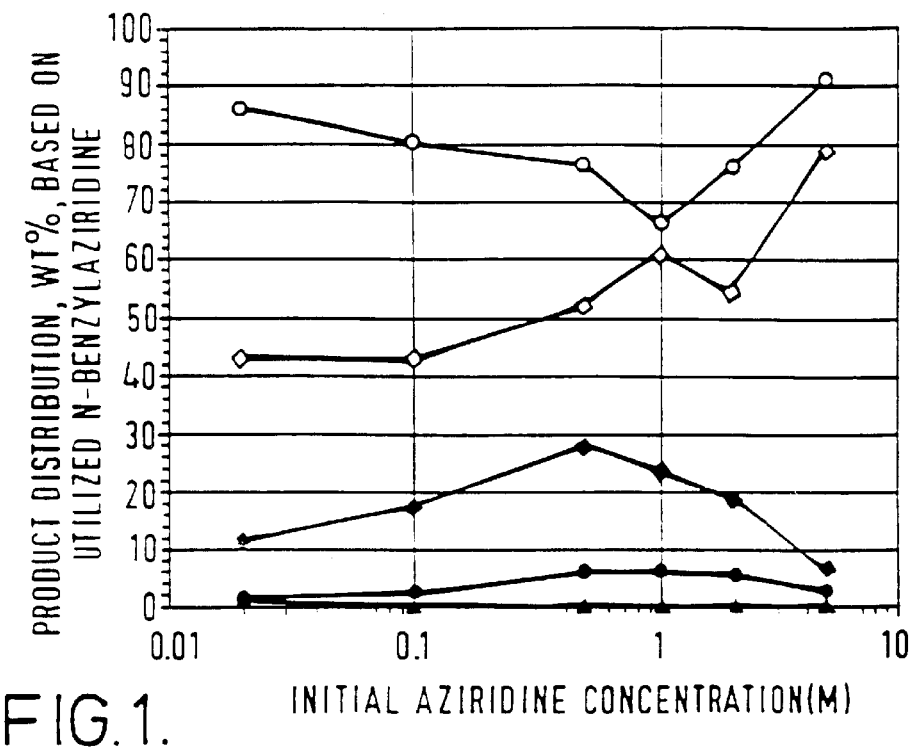
FIG. 1 is a graph showing the effect of initial aziridine concentration on N-benzylaziridine cyclooligomer formation.
Figure 2:
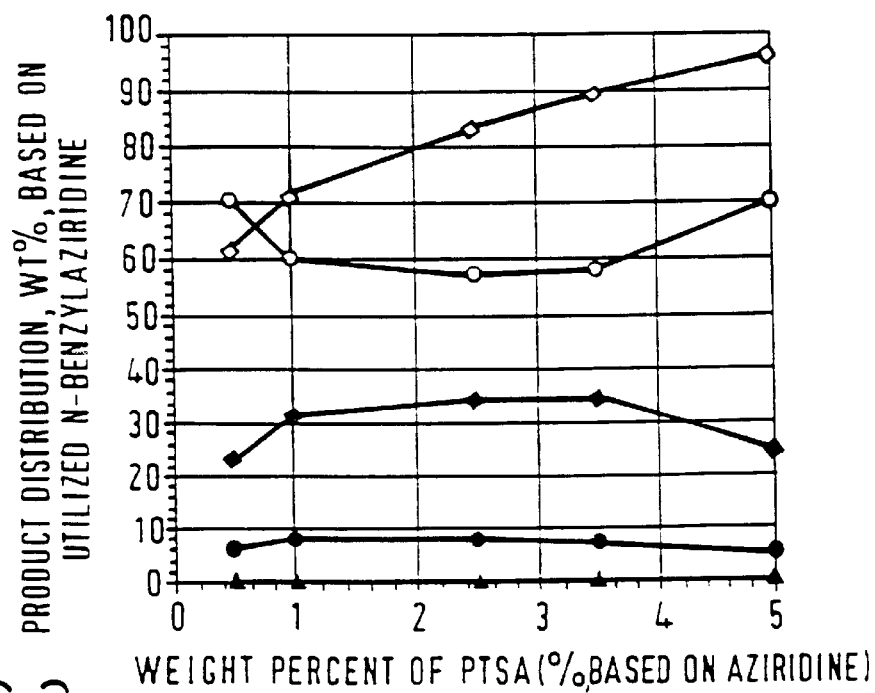
FIG. 2 is a graph showing the effect of initial concentration of the acid catalyst PTSA on N-benzylaziridine cyclooliaomer formation.
Figure 3:
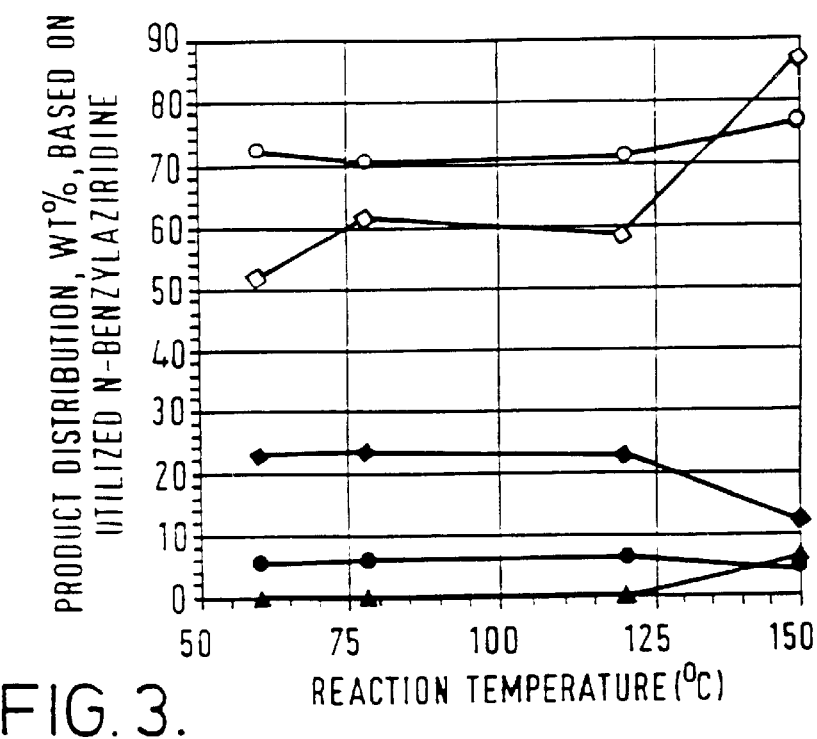
FIG. 3 is a graph showing the effect of reaction temperature on N-benzylaziridine cyclooligomer formation.
Figure 4:
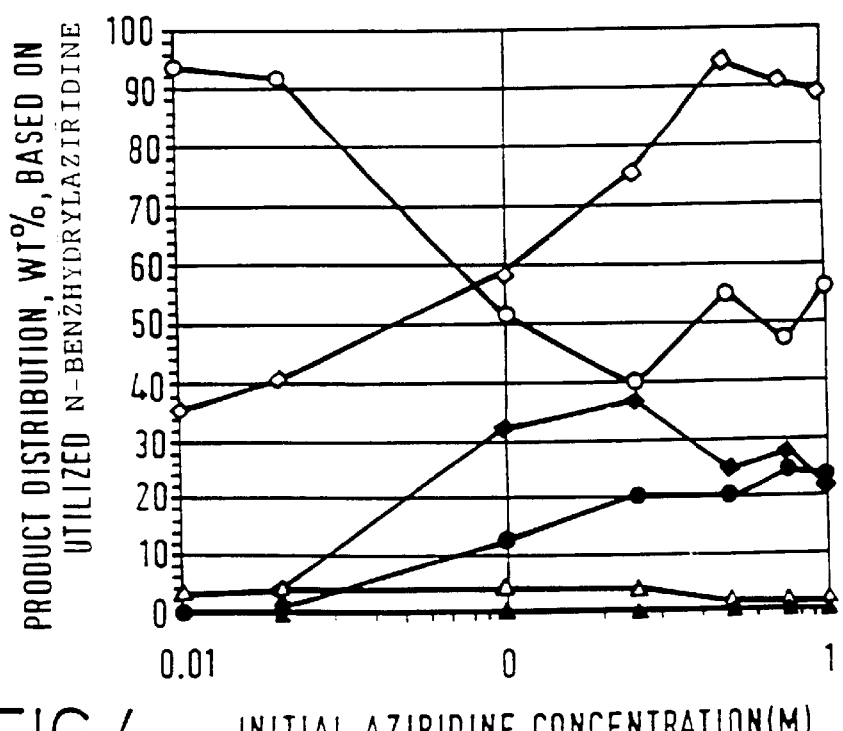
FIG. 4 is a graph showing the effect of initial aziridine concentration on N-benzhydrylaziridine cyclooligomer formation.
Figure 5:
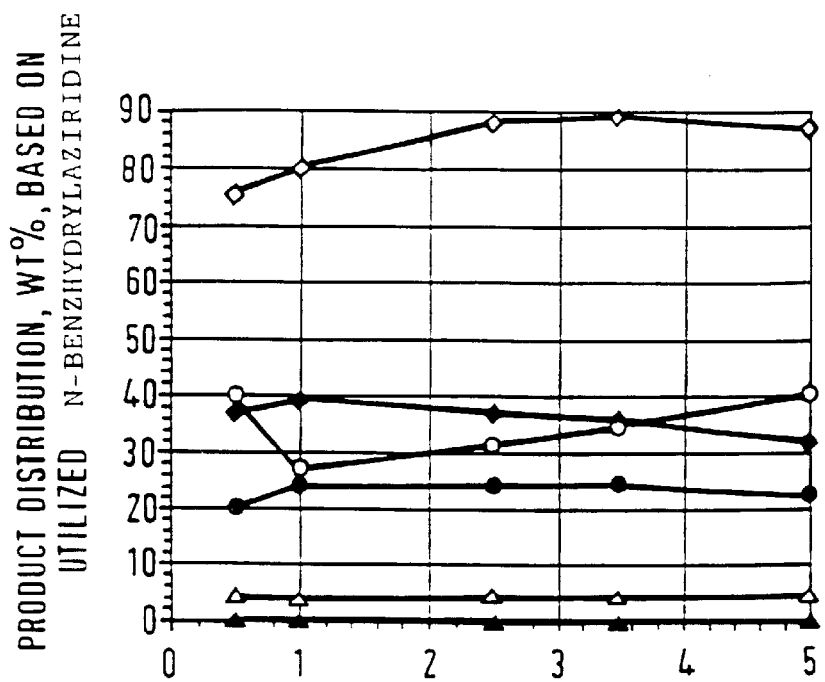
FIG. 5 is a graph showing the effect of initial concentration of the acid catalyst PTSA on N-benzhydrylaziridine cyclooligomer Formation.
Figure 6:
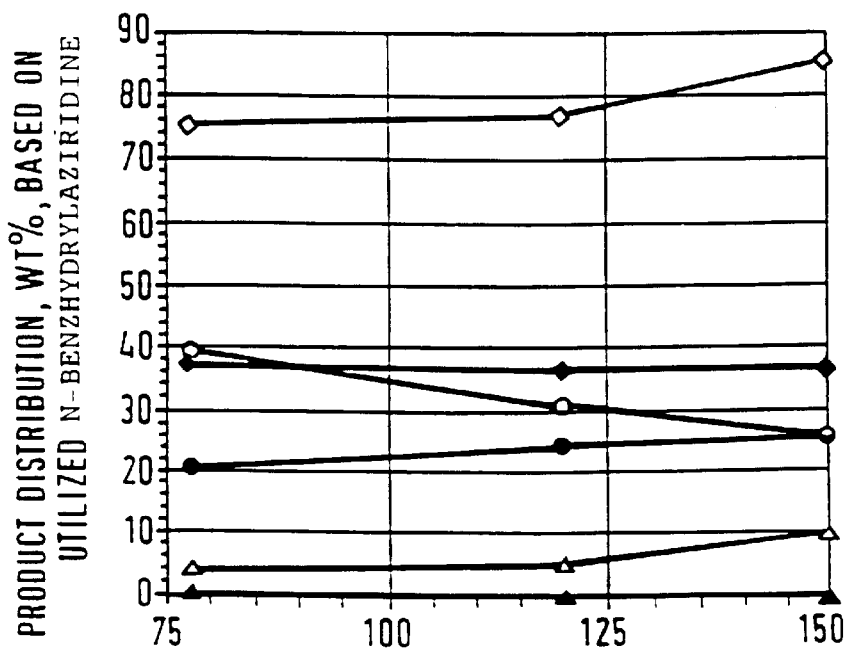
FIG. 6 is a graph showing the effect of reaction temperature on N-benzhydrylaziridine cyclooligomer formation.

In the Figures open diamonds represent converted aziridine, open triangles the cyclic dimer, solid triangles the cyclic trimer, solid diamonds the cyclic tetramer, solid circles the cyclic pentamer and open circles the cyclic hexamer and higher oligomers. FIGS. 1 and 4 are log plots for a reaction mixture containing 0.5 weight % PTSA (relative to the aziridine), 95% ethanol as solvent refluxed for 6 hours. FIGS. 2 and 5 are plots for reaction mixtures containing 1 and 0.25M aziridine respectively, 95% ethanol as solvent, refluxed for 6 hours. FIGS. 3 and 6 are plots for reaction mixtures containing 1 and 0.25M aziridine respectively, 0.5 weight % (relative to aziridine) PTSA, kept for 6 hours at the reaction temperature

EXAMPLE 1

N-Benzylethanoiamine-sulphonate Ester

N-Benzylethanolamine (30.12 g, 0.2 mol from Aldrich) was dissolved in 15 ml of distilled water and the solution was cooled to 0° C. in a salt-ice bath. In a three-neck flask (equipped with a thermometer to measure reaction temperature, magnetic stirbar and air-inlet adaptor) a solution of sulphuric acid was prepared by slow addition of 96.5% sulphuric acid (20.52 g, 0.2 mol) to distilled water (11 ml) with stirring and cooling of the flask in a salt-ice bath. The gas-inlet adaptor was connected to a filter trap, cooled in salt-ice, and the filter flask was connected to a water aspirator. The N-benzyl-ethanolamine solution was then added slowly to the sulphuric acid solution with constant stirring and cooling. The brownish-yellow mixture was heated at 80° C. under water aspiration vacuum. After most of the water was removed, a solid formed and heat was removed. After a few seconds, the reaction mixture solidified and the temperature rose sharply to 140° C. The solid was cooled to ambient temperature and softened with 100 ml of absolute ethanol. The solid was removed from the reaction flask, ground with an additional 50 ml of ethanol and the white sulphonate ester was filtered and dried. Yield 34.3 g (74%). $^1$H NMR ($\delta$, 360 MHz, acetone-$D_6$/$D_2O$): 3.40 (m, 2H, —NC$\underline{H}_2$CH$_2$O—), 4.26 (m, 2H, —NCH$_2$C$\underline{H}_2$O—), 4.36 (2, 2H, —C$\underline{H}_2$Ph), 7.40 (m, 3H, —CH$_2$P$\underline{h}$) and 7.56 (m, 2H, —CH$_2$P$\underline{h}$).

EXAMPLE 2

N-Benzylaziridine

In a three-neck flask (with heating mantle, mechanical stirrer, addition funnel and distillation head with condenser attached to a RB receiver flask containing potassiumn hydroxide pellets and 100 ml of toluene or ether and cooled with an iced bath) N-benzylethanolamine-sulphonate ester (30.7 g, 0.13 mol) was dissolved in 200 ml of water by stirring for 30 minutes at 50° C. The solution was cooled to ambient temperature and then a solution of sodium hydroxide (28.0 g dissolved in 40 ml of water) was added rapidly via the addition funnel to the vigorously stirred ester solution. The reaction mixture was gradually heated and distillate (water and N-benzyl-aziridine) collected in the cooled receiver flask. During the steam distillation, water was added to tee reaction flask whenever the reaction mixture showed signs of crystallizing and bumping. After 2 to 3 hours, the distillation was complete. The distillate was poured into a separation funnel and the toluene/aziridine layer was separated. The aqueous layer was extracted three times with 50 ml of toluene. The toluene phases were combined and dried over sodium hydroxide pellets. The toluene solvent was removed on a roto-vap in the presence of potassium hydroxide pellets. (Ether may be used in place of toluene). The concentrate was vacuum distilled in the presence of KOH pellets using a 7.5 inch Vigreux column. The fraction boiling at 56 to 58° C./2 mmHg was collected and stored over potassium hydroxide pellets. Yield 14.9 g (81% using ether). The procedure of Example 2 required 13 hours. $^1$H NMR ($\delta$, 360 MHz, CDCl$_3$): 1.16 (m, 2H, aziridine ring H), 1.71 (m, 2H, aziridine ring H), 3.27 (s, 2H, —C$\underline{H}_2$Ph), and 7.14 (m, 5H, —CH$_2$P$\underline{h}$); $^{13}$C NMR ($\delta$, 90 MHz, {$^1$H}, CDCl$_3$), 24.5 (aziridine ring C), 64.7 (—$\underline{C}$H$_2$Ph), 126.8, 127.1, 128.1 and 139.4 (—CH$_2$$\underline{Ph}$).

EXAMPLE 3

N,N'N"N'''-Tetrabenzylcyclen (a) N-Benzyl-aziridine (2.05 g, 15.4 mmol) was placed in a 100 ml one-neck roundbottom flask with magnetic stir bar and then 15.5 ml of a solution of p-toluenesulphonic acid monohydrate (PTSA from Aldrich; solution prepared by dissolving 0.253 g PTSA in 37.5 ml of 95% ethanol) was added. A water-cooled condenser was attached. The PTSA thus represented 5% by weight of the N-benzyl-aziridine. The reaction mixture was refluxed for 6 hours and then cooled to ambient temperature. The resulting white solid was filtered and dried and subsequently recrystallized from 150 ml of 2:1 methanol/dichloromethane. Yield 0.78 g (39%). $^1$H NMR ($\delta$, 360 MHz, CDCl$_3$): 2.66 (s, 16H, cyclen ring H), 3.41 (s, 8H, —CH$_2$Ph), and 7.17 (m, 20H, —CH$_2$Ph); $^{13}$C NMR ($\delta$, 90 MHz, {$^1$H}, CDCl$_3$): 53.0 (cyclen ring C), 60.1 (CH$_2$Ph), 126.8, 128.3, 129.2 and 140.4 (CH$_2$Ph); Mass spec (EI, m/e): 532 (M$^+$) mp 144–145° C. (uncorrected).

(b) N-Benzylaziridine (9.0 g, 67.7 mmol) was placed in a 250 ml, one-neck round bottom flask with a magnetic stir bar and then 68.5 mL of 95% ethanol and 0.23 g p-toluenesulfonic acid monohydrate (PTSA from Aldrich) were added. A water-cooled condenser was attached. The PTSA thus represented 2.5% by weight of the N-benzylaziridine. The reaction mixture was refluxed for 6 hours and then cooled to ambient temperature. The resulting white solid was filtered, dried and subsequently recrystallized from about 300 mL of 1:1 methanol/dichloromethane. Isolated yield 3.0 g (33%). $^1$H NMR spectra as in Example 3(a) above.

(c) The title compound was produced in 35.1% yield (33.8 mg) (yield % is based on converted aziridine, by gel permeation chromatography using an internal standard with experimentally determined response factors) by reaction of N-benzylaziridine (0.1 g, 0.75 Tmnol) with 0.75 mL of a solution of p-toluenesulfonic acid [prepared by dissolving 27.0 mg of p-toluenesulfonic acid monohydrate (Aldrich) in 7.5 mL of 95% ethanol] at reflux temperature for 6 hours. The PTSA thus represented 2.5% by weight of the N-benzylaziridine.

N,N',N'',N''',N''''-pentabenzyl-1,4,7,10,13-pentaazacyclopentadecane was obtained in a 6.1% yield (5.8 mg) (from gel permeation chromatography, with yield percentage being based on converted aziridine) from the cyclooligomerization mixture of Example 3 (b).

Cyclic Olicomers of N-benzylaziridine

The yields of cyclic oligomers using the methods of and based on Example 3 were determined by using gel permeation chromatoaraphy. Absolute amounts were determined by comparison to authentic samples of the starting aziridine and the cyclic-(N)$_2$ to cyclic-(N)$_5$ oligomers. The sum of higher oligomers was then obtained by difference.

FIG. 1 of the accompanying drawings shows the yields of macrocyclics as a function of starting material concentration.

FIG. 2 of the accompanying drawings shows the yields of macrocyclics as a function of acid catalyst concentration.

FIG. 3 of the accompanying drawings shows the yields of macrocycles as a function of reaction temperature.

The influence on the yields of different macrocycles, using the methods based on Example 3, of different acid catalysts and different reaction media are shown in Tables 1 and 2 below. Table 1 shows the influence of different catalysts on the cyclooligomer concentrations. Table 2 shows the influence of the reaction medium on the cyclooligomer concentrations.

Table 1 —Influence of Different Acid Catalysts on the Cyclooligomer Fractions (Based on Utilized N-Benzylaziridine, in wt %). (1M, 0.5 wt % catalyst, 6 hour, reflux)

| Catalyst | Aziridine Conversion | c-N$_2$ Yield | c-N$_4$ Yield | c-N$_5$ Yield | >N$_5$ oligomers |
|---|---|---|---|---|---|
| PTSA | 51.7 | 0.3 | 23.6 | 6.0 | 70.2 |
| H$_2$SO$_4$ | 55.9 | 0.0 | 17.0 | 4.7 | 78.3 |
| HOAc | 40.0 | 0.2 | 5.2 | 1.5 | 0.0 |
| H$_3$PO$_4$ | 61.3 | 0.7 | 17.4 | 4.7 | 77.2 |
| HCl | 66.1 | 3.6 | 13.8 | 3.8 | 78.8 |

Table 2 —Influence of Reaction Medium on the Cyclooligomer Fraczions (Based on Utilized N-Benzylaziridine, in wt %). (1M, 0.5 wt % PTSA catalyst, 6 hour, reflux)

| Reaction Medium | Aziridine Conversion | c-N$_2$ Yield | c-N$_4$ Yield | c-N$_5$ Yield | >N$_5$ oligomers |
|---|---|---|---|---|---|
| 95% EtOH* | 51.7 | 0.3 | 23.6 | 6.0 | 70.2 |
| 80% EtOH* | 64.8 | 0.0 | 15.3 | 3.6 | 81.2 |

*balance water

EXAMPLE 4

Cyclen (a) Palladium/charcoal catalyst (0.11 g, Aldrich wet 10% Pd/C, Degussa type El01NE/W), tetra-(N-benzyl)cyclen (0.1 g, 0.18 mmol) and cyclohexene (15 ml of a 1:2 cyclohexene/absolute ethanol mixture obtained using 99% pure cyclohexene from Aldrich) were placed into a one-neck RB flask with a condenser. The mixture was refluxed for 25 hours. The reaction mixture was then filtered by gravity filtration through three layers of S7S#602 fine filter paper and the insolubles were washed with three 10 mL portions of ethanol. The combined filtrates were roto-vaped to produce the title compound. Yield 0.028 g (88%).

(b) Tetrabenzylcyclen (0.5 g, 0.9 mmol), ethanol (50 mL), and 10% Pd on carbon (0.5 g) were loaded into a 100 ml Autoclave pressure reactor. The reactor was pressurized to 100 psig with hydrogen for 3 hours at 80° C. The mixture was filtered to remove the catalyst and the filtrate was concentrated to afford pure cyclen in essentially quantitive yield (m/e=172). $^1$H NMR ($\delta$, 360 MHz, CDCl$_3$): 2.35 (bs, 4H, —NH) and 2.67 (s, 16H, —NCH$_2$CH$_2$N—); $^{13}$C NMR ($\delta$, 90 MHz, {$^1$H}, CDCl$_3$): 46.1 (—NCH$_2$CH$_2$N—).

EXAMPLE 5

1,4,7,10-Tetra-carboxymethyl-1,4,7,10-tetraazacyclododecane (DOTA)

To an aqueous solution of cyclen (0.16 mols in 58 mL water) was added an aqueous solution of sodium chloroacetate (0.71 mols sodium chloroacetate in 68 mL of water). This solution was stirred at 80° C. overnight while maintaining the pH at 9–10. After cooling to ambient temperature the pH of the solution was adjusted to 2.5 with aqueous HCl. The resulting precipitate was collected by filtration washed with acetone and dried in vacuo to afford 45.5 g of DOTA-HCl (m/e=628).

EXAMPLE 6

Sodium Salt of the 1,4,7,10-tetra-carboxymethyl-1,4,7,10-tetraazacycododecane (DOTA) gadolinium (III) Complex To 300 mL of water was added 9.3 g Gd$_2$O$_3$ (0.0256 mols) and 0.051 mols of DOTA. The solution was warmed to 90°

C. and the pH was adjusted to 8–9. The solution was cooled to ambient temperature and the pH was adjusted to 7.5 with HCl. The product was precipitated with acetone, collected by filtration, and then dried in vacuo to afford 26.0 g of white product.

EXAMPLE 7

N-Benzhydryl-ethanolamine

In a 500 mL round bottom flasK equipped with a condenser and a thermometer, 2-choroethan-1-ol (23.3 grams, 0.39 mol, Kodak), α-aminodinhenyimethane (82.0 grams, 0.45 mol, Fluka), and water (17 mL) were placed. The mixture was heated on a steam bath (ca. 90° C.) for six hours. After cooling to ambient temperature, NaOH (15 grams, 0.37 mol) was added and the mixture heated on a steam bath for 45 minutes at ca. 90° C. Water (50 mL) was then added to the solution. The resulting two-layered mixture was extracted with two 50 mL portions of toluene. The combined toluene extracts were dried over sodium hydroxide pellets and the toluene then removed by rotary evaporation at reduced pressure. The residue was fractionally distilled using a 7.5 inch Vigreux column. The fraction boiling at 175–177° C./2 mm pressure was collected and then recrystallized from hexane. Yield 39.0 g (59% yield). $^1$H NMR (δ, 360 MHz, CDCl$_3$): 2.32 (bs, 2H, —OH & —NH), 2.74 (m, 2H, —NC$\underline{H}_2$CH$_2$O—), 3.64 (m, 2H, —NCH$_2$C$\underline{H}_2$O—), 4.84 (s, 1H, C$\underline{H}$Ph$_2$) and 7.30 (m, 10H, aromatic H); $^{13}$C NMR (δ, 90 MHz, {$^1$H}, CDCl$_3$); 49.5 (—N$\underline{C}$H$_2$CH$_2$O—), 61.5 (—NCH$_2$$\underline{C}$H$_2$O—), 67.0 ($\underline{C}$HPh$_2$), 127.2, 127.3, 128.3 and 147.5 (CH$\underline{Ph}_2$). mp 69–70° C. uncorrected.

EXAMPLE 8

N-Benzhydryl-ethanolamine Sulphonate Ester

A suspension of N-benzhydryl-ethanolamine (24.8 grams, 0.11 mol) was prepared in a 500 mL three-neck round bottom flask (equipped with a thermometer, magnetic stir bar, and air-inlet adapter) in 60 mL of distilled water and the mixture cooled to 0° C. in an ice bath. A sulphuric acid solution (11.9 grams of sulphuric acid, 0.12 mol, dissolved in 10 mL of distilled water) was added slowly with constant stirring and cooling of the flask in the ice bath. The ice bath was removed and the resulting clear yellow solution was heated under water aspirator vacuum. After most of the water had been removed by evaporation, the solution thickened and the temperature rose steadily. After the temperature rose to 180° C., the solution darkened in colour. The heat source was immediately removed and the mixture was allowed to cool to ambient temperature, yielding a golden brown glassy material. Distilled water (50 mL) was added, and the mixture was stirred at ambient temperature for 1.5 hours until the glassy residue had changed to an off-white powdery solid. The solid was filtered and washed with several mL of acetone. Yield 2.9 g (41% yield). $^1$H NMR (δ, 360 MHz, acetone-D$_6$/D$_2$O): 3.24 (m, 2H, —NC$\underline{H}_2$CH$_2$O—), 4.20 (m, 2H, —NCH$_2$C$\underline{H}_2$O—), 5.56 (s, 1H, C$\underline{H}$Ph$_2$), 7.36 (m, 10H, —CH$\underline{Ph}_2$).

EXAMPLE 9

N-Benzhydryl-aziridine

A suspension of N-benzhydryl-ethanolamine sulphonate ester (13.6 grams, 44.3 mmol) in distilled water (140 mL) was placed in a 500 mL three-necked flask fitted with an addition funnel and mechanical stirrer. The mixture was heated to ca. 50° C. and stirred until most of the solid had dissolved. A solution of sodium hydroxide (8.7 grams, 220 mmol) in distilled water (30 mL) was then added with vigorous stirring. Toluene (100 mL) was added to the mixture and the resulting two-phase mixture was stirred vigorously for one hour while cooling to ambient temperature. The mixture was poured into a separatory funnel and the toluene/N-benzhydryl-aziridine layer was removed. The aqueous layer was extracted three times with 50 mL portions of toluene. The combined toluene solutions were dried over NaOH pellets. The toluene solvent was removed on a rotary evaporator at reduced pressure and the crude. product was recrystallized from hexane. (Alternatively one may use ether rather than toluene: here the reaction mixture, after the addition of 30 mL distilled water was gradually heated and distillate (water and N-benzhydryiaziridine) collected in the cooled receiver flask. After about 3–4 hours, (when the distillate contained no more oil drops), distillation was stopped and the reaction mixture was allowed to cool to ambient temperature. The distillate was poured into a separatory funnel and mixed with 100 mL ether. The aziridine-ether layer was separated. The aqueous layers from the distillate and the cooled reaction mixture were extracted twice with ether. The ether phases were corbined and dried over sodium hydroxide pellets. The ether solvent was removed on a rotary evaporator at reduced pressure and the crude product was recrystallized from hexane.) Yield 6.2 g (66%). $^1$H NMR (δ, 360 MHz, CDCl$_3$): 1.33 (m, 2H, aziridine ring H), 1.87 (m, H, aziridine ring H), 3.33 (S, H, C$\underline{H}$Ph$_2$), and 7.26 (m, 5H, CH$\underline{Ph}_2$); $^{13}$C NMR (δ, 90 MHz, {$^1$H}, CDCl$_3$) 28.1 (aziridine ring C), 78.9 ($\underline{C}$HPh$_2$), 127.1, 127.4, 128.4 and 143.3 (CH$\underline{Ph}_2$). mp 56–58° C. uncorrected. Mass spectrum (EI, m/e): 209 (M$^+$).

EXAMPLE 10

N,N',N'',N'''-Tetrabenzhydryl-cyclen (a) Analogously to Example 3, the title compound was produced in 40% crude yield (25% relative yield by gel permeation chromatography using an internal standard with experimentally determined response factor) by reaction of N-benzhydryl-aziridine (78.6 mg, 0.37 mmol) with 0.5% by weight of PTSA in ethanol (4 mL). $^1$H NMR (δ, 360 MHz, CDCl$_3$): 2.75 (s, 16H, cyclen ring H), 4.62 (s, 4H, —C$\underline{H}$Ph$_2$), and 7.13 (m, 40H, CH$\underline{Ph}_2$); Mass spec (EI, m/e): 837 (M$^+$). mp 200–202° C. uncorrected.

The title product tetramer can be deprotected, alkylated and metallated analogously to the tetrabenzyl-cyclen reactions of Examples 4 to 6.

N,N',N'',N''',N''''-Pentabenzhydryl-1,4,7,10,13-pentaazacyclopentadecane was obtained in 13.7% relative yield (gel permeation chromatography) from the reaction mixture of Example 10. $^1$H NMR (δ, 360 MHz, CDCl$_3$): 3.04 (s, 20H, macrocycle ring H), 4.52 (s, 5H, C$\underline{H}$Ph$_2$), and 7.15 (m, 50H, CH$\underline{Ph}_2$).

(b) Analogously to Example 3, for the synthesis of a pure sample of the title compound in a preparative scale the following procedure was used. N-benzhydryl-aziridine (2.2 g, 10.5 mmol) with 0.35% by weight of p-toluenesulfonic acid (7.8 mg, 0.041 mmol, Aldrich) were reacted in 95% ethanol (25 mL) After cooling the reaction mixture to ambient temperature, the precipitated solid was filtered off and suspensed in about 200 mL of ethanol. The suspension was filtered and the insoluble material was collected and dried. Isolated yield 0.1 g (5%).

$^1$H NMR (δ, 360 MHz, CDCl$_3$): 2.75 (s, 16H, cyclen ring H), 4.62 (s, 4H, —C$\underline{H}$Ph$_2$), and 7.13 (m, 40H, CH$\underline{Ph}_2$); Mass spec (EI, m/e): 837 (M$^+$). mp 200–202° C. uncorrected.

The title compound was produced in 41.1% yield (26.9 mg) (yield % based on converted aziridine, gel permeation chromatography using an internal standard with experimentally determined response factor) by reaction of N-benzhydrylaziridine (78.7 mg, 0.37 mmol), 0.6 mL of a solution of p-toluenesulfonic acid [prepared by dissolving 27.0 mg of p-toluenesulfonic acid monohydrate (Aldrich) in 7.5 mL of 95% ethanol] and 0.9 mL of 95% ethanol at reflux temperature for 6 hours. The PTSA thus represented 2.5% by weight of N-benzhydrylaziridine.

The title product tetramer can be deprotected, alkylated and metallated analogously to the tetrabenzyl-cyclen reactions of Examples 4 to 6.

N,N',N'',N''',N''''-pentabenzhydryl-1,4,7,10,13-pentaazacyclopentadecane was obtained in 26.5% yield (16.9 mg) based on converted aziridine (from gel permeation chromatography) from the cyclooligomerization reaction mixture of Example 10(b). $^1$H NMR (δ, 360 MHz, CDCl$_3$): 3.04 (s, 20H, macrocycle ring H), 4.52 (s, 5H, CEPh$_2$), and 7.15 (m, 50H, CHPh$_2$). Mass spectrum (FAB, 3-nitrobenzyl alcohol, m/e): 1046.4 (M$^+$), mp 208–210° uncorrected.

It has been shown that there is a large difference in the cyclooligomer distribution in the product mixtures obtained from stoichiometric and catalytic protonation. A GPC chromatogram obtained on a reaction mixture from stoichiometric protonation (with PTSA) showed the presence of large amounts of cyclopentamer and cyclohexamer along with trace amounts of cyclodimer, cyclotetramer, higher oligomers or cyclooligomers, and unreacted N-benzylhydrylaziridine.

FIG. 4 of the accompanying drawings shows the N-benzhydryl cyclooligomerization as a function of initial aziridine concentration.

FIG. 5 of the accompanying drawings shows the N-benzhydryl cyclooligomerization as a function of acid concentration (PTSA).

FIG. 6 of the accompanying drawings shows the N-benzhydryl cyclooligomerization as a function of the reaction temperature.

EXAMPLE 11

N,N',N'',N''',N'''',N'''''-hexabenzhydryl-1,4,7,10,13,15-hexaazacyclohexadecane

In a 20 mL vial, a mixture of N-benzhydrylaziridine (78.6 mg, 0.37 mmol) and p-toluene-sulfonic acid monohydrate (71.5 mg, 0.37 mmol, Aldrich) were dissolved in 2.5 mL dichloromethane (dried via distillation from P$_2$O$_5$). In another vial, N-benzhydrylaziridine (156 mg, 0.74 mmol) was dissolved in 1.0 mL of dichloromethane. Both solutions were transferred into two separate addition funnels attached to a 50 mL three-neck flask (equipped with a water-cooled condenser and a stir bar) containing 1.0 mL of dichloromethane. Both solutions were added simultaneously into the flask with vigorous stirring. After the mixture had been refluxed for 6 hours, a white solid was obtained upon the removal of the solvent by rotary evaporation at reduced pressure. The GPC analysis of the product mixture indicated the presence of title compound approximately in 59% yield based on utilized aziridine. Other by-products included N,N',N'',N''',N''''-pentabenzhydryl-1,4,7,10,13-pentaazacyclopentadecane (31.3%) cyclodimer (5.3%), cyclotetramer (31.3%) and trace amounts of higher oligomers or cyclooligomers (% yields by gel permeation chromatography based on utilized aziridine).

TABLE 3

| Aziridine conversion, % | c-N$_2$ % | c-N$_4$ % | c-N$_5$ % | >c-N$_5$ (mostly c-N$_6$), % |
|---|---|---|---|---|
| 91.3 | 5.3 | 3.9 | 31.3 | 59.5 |

EXAMPLE 12

1,7-bis(N-benzyl)-1,4,7,10-tetraazacyclododecane

Analogously to Example 4, the title compound was obtained by reacting tetra(N-benzyl)cyclen (100 mg) and 15 mL of 1:2 v/v cyclohexane/ethanol solution in the presence of 5% Pd on alumina catalyst (Aldrich). $^1$H NMR (δ, 360 MHz, CDCl$_3$): 2.57 (AA'BB' spin system, 16H, cyclen ring H), 3.55 (s, 4H, CHPh), and 7.30 (m, 10H, CH$_2$Ph); Mass spec (EI, m/e): 352 (M$^+$).

EXAMPLE 13

1,4,7-tri(N-benzyl-triazacyclononane (Tribenzyl, TACN)

In a 20 ml vial, a mixture of N-benzylaziridine (79.0 mg, 0.59 mmol), p-toluenesulphonic acid (116.0 mg, 0.59 mmol) and 5 ml of methylene chloride were stirred until all acid dissolved. In another vial, N-benzylaziridine (158.0 mg, 1.18 mmol) was dissolved in 5 ml of methylene chloride. Both of these solution were added simultaneously with vigorous stirring into a 50 ml three-neck flask (equipped with two addition funnels, a water-cooled condenser and a stir bar) containing 1 ml of methylene chloride. After the mixture had been refluxed for 4 hours, an off-white semi-solid was obtained after removing the solvent by rotary evaporation a: reduced pressure. The product contained a mixture of cyclic dimer, trimer, tetramer, pentamer and other higher oligomers with the trimer being the most predominant product by $^1$H NMR. The $^1$H NMR values were consistent with the assigned cyclic trimer ($^1$H NMR: 2.90(s) and 3.62(s); integral ratio 2:1). The various polymers may be separated out by column chromatography.

EXAMPLE 14

Mixed Aziridine Cocyclization

In a 20 ml vial, a mixture of N-benzylaziridine (0.05 grams, 0.38 mmol) p-toluenesulphonic acid (0.071 grams, 0.39 mmol) and 3 ml of chloroform were stirred until all acid dissolved. In another vial, N-benzhydrylaziridine (0.23 grams, 1.18 mmol, 3 equivalents) was dissolved in 1 ml of chloroform. Both of these solution were transferred into two separate addition funnels attached to a 50 ml three-neck flask (equipped with a water-cooled condenser and a stir bar). Both solutions were added simultaneously into the flask with vigorous stirring. After the mixture had been refluxed for 5 hours, a white solid was obtained after removing the solvent by rotary evaporation at reduced pressure. The $^1$H NMR spectral data indicated the absence of N-benzylaziridine, presence of some N-benzhydrylaziridine, and new resonances between 2–3 ppm and 4–5 ppm indicative of a mixed N-alkylated cyclooligomer.

EXAMPLE 15

1,4,7-Triazacyclononane (TACN)

Tribenzyl.TACN, ethanol, and 10% Pd on carbon are loaded into a 100 mL Autoclave pressure reactor. The reactor is pressurized to 100 psig with hydrogen for 3 hours at 80° C. The mixture is filtered to remove the catalyst and the filtrate is concentrated to afford pure TACN in essentially auantitatve yield.

EXAMPLE 16

1,4,7-Tricarboxyethyl-1,4,7-trazacyclononane

To an aqueous solution of TACN (0.16 mols in 58 mL water) is added an aqueous solution of sodium chloroacetate (0.71 mols sodium chloroacetate in 68 mL of water). This solution is stirred at 80° C. overnight while maintaining the pH at 9–10. After cooling to ambient temperature the pH of the solution is adjusted to 2.5 with aqueous HCl. The resulting precipitate is collected by filtration, washed with acetone, and dried in vacuo to afford the monohydrochloride salt of 1,4,7-tricarboxymethyl-1,4,7-triazacyclononane.

EXAMPLE 17

N-(4-Methylbenzyl)ethanolamine

The procedure of Example 7 was repeated using 2-chloroethanol (20.9 g, 0.26 mol, Kodak), 4-methylbenzylamine (32.7 g, 0.27 mol, Aldrich), water (25 mL) and KOH (14.6 g, 0.26 mol). A white solid was crystallized from the concentrated solution. The crystallized product was collected by suction filtration and recrystallized from hexanes. The filtrate was concentrated under reduced pressure and the residue was fractionally distilled using a 7.5 inch vigreux column. The fraction boiling at 140–1440° C./9 mm pressure was collected. Total yield 15 g (35% yield). $^1$H NMR ($\delta$, 360 MHz, CDCl$_3$) 2.32 (s, 3H), 2.51 (broad s, 2H), 2.74 (t, 2H), 3.61 (t, 2H), 3.72 (s, 2H) and 7.142 (m, 4H) $^{13}$C NMR ($\delta$, 90 MHz, {$^1$H}, CDCl$_3$): 21.0 (—CH$_3$) 50.5 (—NCH$_2$CH$_2$O—), 53.2 (—NCH$_2$CH$_2$O—), 60.7 (—NCH$_2$Ph), 128.1, 129.1 and 143.0 (—CH$_2$Ph). mp 61–62° C. uncorrected. The title compound was also prepared using the following procedure. In a 2L three-neck flask (equipped with a mechanical stirrer and an addition funnel) ethanolamine (91.6 g, 1.5 mol, Aldrich) and 100 mL of toluene were placed. To this solution was added dropwise 4-methylbenzyl chloride (70.3 g, 0.5 mol, Aldrich). The mixture was stirred for 10 hours at room temperature. Crushed KOH (30.0 g, 0.5 mol) was added and stirring was continued for another 3 hours. Water (300 mL) was added to dissolve all solid. The mixture was poured into a separatory funnel and the toluene layer was separated. The aqueous layer was extracted with 50 mL portions of methylene chloride three times. The combined extracts were dried on anhydrous sodium sulfate and rotovaped to remove the solvents. A white solid was crystallized from the concentrated solution. The crystallized product (34 g) was collected by suction filtration and washed with several mL of toluene. The filtrate was concentrated under reduced pressure and the residue was fractionally distilled using a 7.5 inch vigreux column. The fraction boiling at 140–144° C./9 mm pressure was collected. Total yield isolated 46.5 g (57% yield).

EXAMPLE 18

N-(4-Methylbenzyl)ethanolamine Sulphonate Ester

A suspension of 4-methylbenzylethanolamine (6.0 g, 36.3 mmol) was prepared in a 250 mL three-neck flask (equipped with a thermometer, magnetic stir bar and air inlet adapter) in 3. 0 mL distilled water and the mixture was cooled to 0° C. in an ice bath. A solution of sulfuric acid (3.56 g, 36.3 mmol, dissolved in 1.8 7 water) was added slowly to the flask with constant stirring and cooling in the ice bath. The reaction mixture was then heated under water aspirator vacuum. After most of the water was removed at 55° C., a solid formed and the heat source was removed. After a few seconds, the reaction mixture solidified and the temperature rose sharply to 130° C. The solid was cooled to ambient temperature and softened with 50 mL of absolute ethanol. The solid was removed from the flask, ground in ethanol and the sulphonate ester was filtered and dried. Yield 6.8 g (76.5% yield). $^1$H NMR ($\delta$, 360 MHz, Acetone-D$_6$/D$_2$O): 2.22 (s, 3H), 3.31 (t, 2H), 4.19 (t, 2H), 4.21 (s, 2H) and 7.25 (m, 4H). Decomposed at 247° C.

EXAMPLE 19

N-(4-Methylbenzyl)aziridine

Analogously to Example 2, the title compound was synthesized in 93% yield (3.8 g) using N-(4-methylbenzyl) ethanolamine sulphonate ester (6.8 g, 2.7 mmol, dissolved in 150 mL of distilled water) and a solution of sodium hydroxide (6.07 g dissolved in 10 mL of water). $^1$H NMR ($\delta$, 360 MHz, CDCl$_3$): 1.25 (t, 2H), 1. 79 (t, 2H), 2.30 (s, 3H), 3.33 (s, 2H) and 7 .18 (m, 4H).

EXAMPLE 20

N,N',N",N'"-Tetra(4-methylbenzyl)cyclen

The title compound was produced in 40.3% yield by reaction of N-(4-methylbenzyl)aziridine (0.1 g, 0.7 mmol) with 2.5% by weight of PTSA in ethanol (0.35 mL) at reflux temperature for 6 hours. The other by-products contained cyclodimer (4.8%), cyclotrimer (0.2%), cyclopentamer (8.5%), and other higher oligomers and cyclooligomers % yields are the relative product ratios by gel permeation chromatography).

EXAMPLE 21

Comparative Degrees of Cyclooligomerization in Examples 3 and 20

Table 4 shows the change in relative cyclooligomer product ratios as a function of substituent on the nitrogen of the aziridine.

Table 4 —Relative Product Ratios of Cyclooligomers (Based on Area % from GPC Chromatogram, in %). (1M, 2.5 wt % PTSA catalyst, 6 hour, reflux)

| Aziridine | c-N$_2$ Yield | c-N$_3$ Yield | c-N$_4$ Yield | c-N$_5$ Yield | >c-N$_5$ oligomers |
|---|---|---|---|---|---|
| N-Benzyl | 0.6 | 0.0 | 63.4 | 9.7 | 14.1 |
| N(4-methyl benzyl | 4.8 | 0.2 | 40.3 | 8.5 | 53.8 |

What is claimed is:

1. A compound of formula II

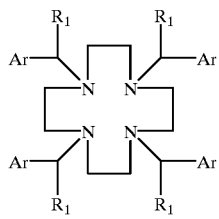

(II)

where Ar is an optionally substituted phenyl group and each $R_1$ is independently hyrogen or an Ar group and at least two differing $ArCHR_1$ moieties are present.

2. A compound as claimed in claim 1 wherein one $ArCHR_1$ moiety is benzyl and three are benzhydryl.

3. A compound as claimed in claim 1 wherein three $ArCHR_1$ moieties are benzyl and one is benzhydryl.

* * * * *